(12) United States Patent
Wilson et al.

(10) Patent No.: US 6,660,248 B2
(45) Date of Patent: Dec. 9, 2003

(54) FULLERENE ($C_{60}$)-BASED X-RAY CONTRAST AGENT FOR DIAGNOSTIC IMAGING

(75) Inventors: Lon J. Wilson, Houston, TX (US); John T. Wharton, Houston, TX (US); Uri Sagman, Toronto (CA)

(73) Assignee: William Marsh Rice University, Houston, TX (US)

( * ) Notice: Subject to any disclaimer, the term of this patent is extended or adjusted under 35 U.S.C. 154(b) by 63 days.

(21) Appl. No.: 10/038,075

(22) Filed: Nov. 9, 2001

(65) Prior Publication Data

US 2002/0164288 A1 Nov. 7, 2002

Related U.S. Application Data

(60) Provisional application No. 60/247,337, filed on Nov. 10, 2000.

(51) Int. Cl.[7] ................. A61K 51/00; A61K 49/00; C01B 31/00
(52) U.S. Cl. ............... 424/9.4; 424/9.42; 424/9.45; 423/445 B; 516/901
(58) Field of Search ................. 424/9.4, 9.45, 424/9.451, 9.455, 9.42, 9.3; 423/445 B, DIG. 39, DIG. 40; 516/901

(56) References Cited

U.S. PATENT DOCUMENTS

| 4,314,055 A | 2/1982 | Hoey et al. ............... 536/53 |
| 4,978,793 A | 12/1990 | Quirk et al. .............. 564/487 |
| 5,248,498 A | 9/1993 | Neumann et al. ........... 424/9 |
| 5,688,486 A | 11/1997 | Watson et al. ............ 424/1.65 |
| 5,739,376 A | 4/1998 | Bingel .................... 560/51 |

FOREIGN PATENT DOCUMENTS

| BE | 836 355 | 12/1975 | |
| BE | 846 657 | 9/1976 | |
| BE | 882 309 | 3/1980 | |
| DE | 20 31 724 | 6/1970 | ....... C07C/103/38 |
| DE | 24 56 685 A1 | 12/1973 | ....... C07C/103/76 |
| DE | 29 09 439 A1 | 3/1979 | ....... C07C/103/78 |
| DE | 30 01 292 A1 | 1/1980 | ....... C07C/103/76 |
| DE | 3407 473 C2 | 2/1984 | ........ C07K/5/06 |
| EP | 0 026 281 | 8/1979 | ....... C07C/103/78 |
| EP | 0 022 056 | 1/1981 | ....... C07C/149/23 |
| EP | 0 033 426 | 8/1981 | ....... C07D/321/06 |
| EP | 0 049 745 | 4/1982 | ....... C07C/103/78 |
| EP | 0 083 964 | 7/1983 | ....... C07C/103/78 |
| EP | 0 105 752 | 4/1984 | ....... C07C/103/78 |
| EP | 0 0108 638 | 5/1984 | ....... C07C/103/78 |
| EP | 0 153 992 | 9/1985 | ......... C07C/5/06 |
| GB | 1 548 594 | 6/1977 | ........ A61K/29/02 |
| WO | WO 87/00757 | 2/1987 | ........ A61K/49/04 |

OTHER PUBLICATIONS

Article entitled: *"New non–ionic, highly water–soluble derivatives of C60 designed for biological compatibility,"* by Tim Wharton et al., Department of Chemistry and the Center for Nanoscale Science and Technology, MS–60 Rice University, Houston, pp. 5159–5162, Jun. 4, 2001.

Article entitled: *"Experimental and theoretical x–ray imaging performance comparison of iodine and lanthanide contrast agents,"* by H. Neale Cardinal et al., The John P. Roberts Research Laboratories, received Mar. 30, 1992, published Jul. 15, 1992, pp. 15–31.

Article entitled: *"Toward fullerene–based x–ray contrast agents: design and synthesis of non–ionic, highly–iodinated derivatives of $C_{60}$,"* by Tim Wharton and Lon J. Wilson, Department of Chemistry and the Center for Nanoscale Science and Technology, MS–60 Rice University, Houston, Tetrahedron Letters, pp. 1–5, 2001 Elsevier Science.

Article entitled: *"Medical applications of fullerenes and metallofullerenes,"* by Lon J. Wilson, The Electrochemical Society *Interface*, 1999, pp. 24–28.

*Primary Examiner*—Michael G. Hartley
(74) *Attorney, Agent, or Firm*—Conley Rose, P.C.

(57) ABSTRACT

An contrast agent for therapeutic or diagnostic treatment comprises a fullerene scaffold and an iodinated moiety bonded to the scaffold. The agent may further comprise a water solubilizing moiety bonded to the scaffold, which may be a serinol malonodiamide, hydroxyl, and 1,3-diol. The fullerene scaffold may comprise an empty fullerene or an endohedral fullerene. A method for making the agent includes a) synthesizing iodinating moieties, b) protecting serinols, forming protected serinols, c) attaching the protected serinols to the iodinated moieties, forming iodinated serinols, d) attaching the iodinated serinols to the fullerene scaffold, and, optionally, d) de-protecting the serinols. Also disclosed are a method for providing diagnostic treatment to a patient comprising administering to said patient a radiopaque effective amount of a contrast agent comprising a fullerene scaffold and an iodinated moiety, a method of making a blood pool agent.

38 Claims, 7 Drawing Sheets

PRIOR ART

FULLERENE ($C_{60}$)-BASED X-RAY CONTRAST AGENT FOR DIAGNOSTIC IMAGING

CROSS-REFERENCE TO RELATED APPLICATIONS

This application claims benefit of priority of U.S. provisional application Ser. No. 60/247,337, filed Nov. 10, 2000, and entitled "Fullerene ($C_{60}$)-Based X-Ray Contrast Agent for Diagnostic Imaging," which is incorporated herein by reference.

STATEMENT REGARDING FEDERALLY SPONSORED RESEARCH OR DEVELOPMENT

Not Applicable.

FIELD OF THE INVENTION

This invention relates to a new contrast agent for medical use in diagnostic x-ray imaging and method for making the same. The compound comprises an x-ray contrast agent based on a fullerene ($C_{60}$) scaffolding material.

BACKGROUND OF THE INVENTION

Since the fortuitous discovery of X-rays by Wilhelm C. Röntgen in 1895, X-ray radiography has evolved into the foundation of contemporary medical imaging. The term "X-ray radiography" can be taken to encompass all of the technology involved in the creation of medically useful images, from the production of X-ray radiation to the processing of raw photographic, or more recently, digital data. Although the past two decades have experienced an explosive growth in ultrasound and magnetic resonance imaging (MRI) modalities (due largely to the advent of the microchip), approximately 75–80% of all imaging procedures still entail the use of X-rays.

Figure 1:
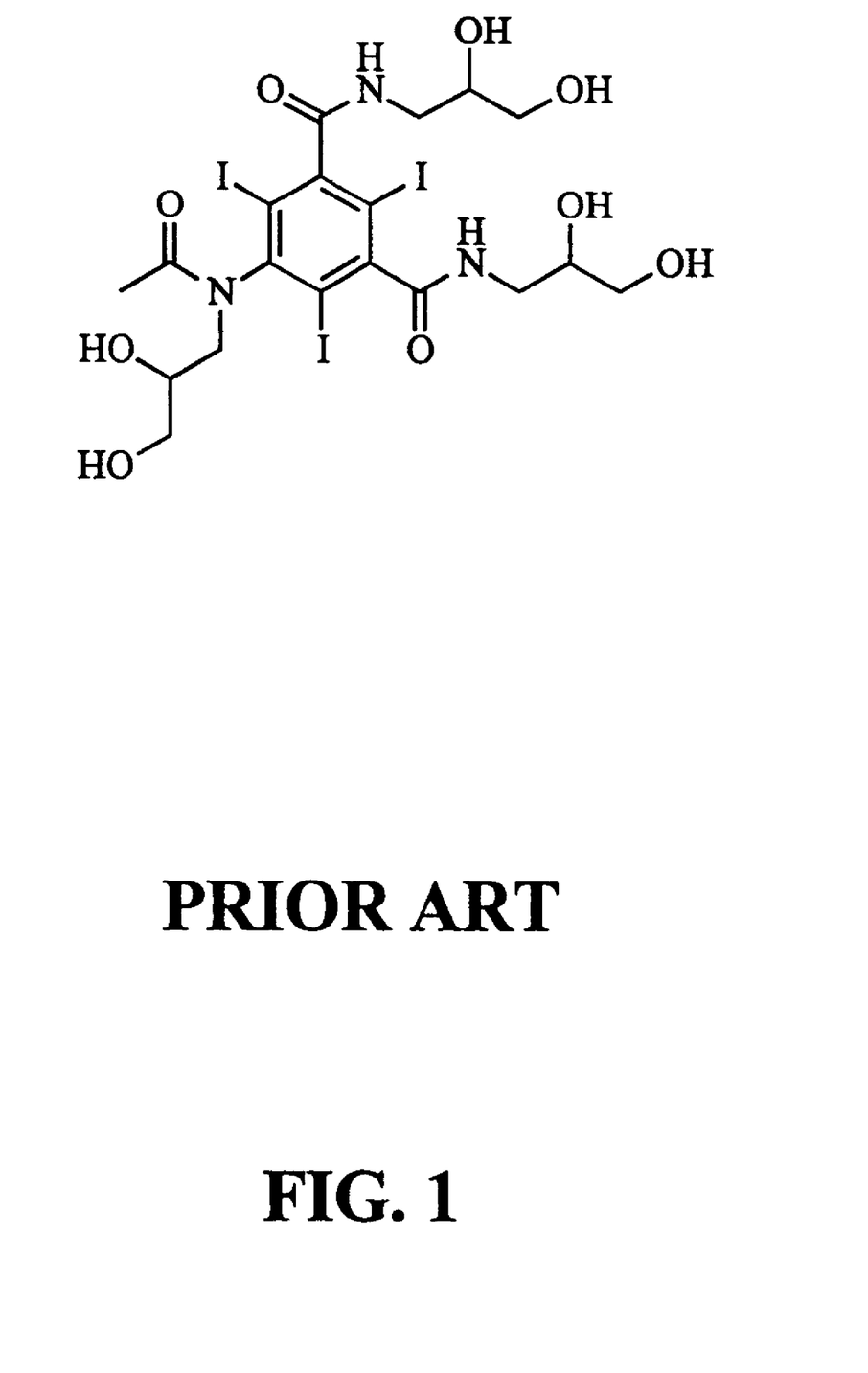
FIG. 1 is a schematic drawing of the chemical structure of Iohexal.

Contemporary X-ray radiography is intimately dependant upon the use of X-ray contrast agents (also called X-ray contrast media, radiopaque agents, and roentgenographic agents). With the exception of orally ingested barium salt slurries for gastrointestinal imaging, all commonly employed X-ray contrast agents (CA) are based on the 1,3,5-triiodinated-5-aminoisophthalic acid substructure. The substructure, along with a typical, commercially available X-ray contrast agent, Iohexol, is shown in FIG. 1. Administered intravenously, the agents enhance radiographic image contrast by increasing x-ray attenuation via their multiple electron-rich iodine atoms. In the U.S. alone, iodinated contrast agents are used in approximately 20 million procedures annually.

The fractional decrease in X-ray radiation intensity (X-ray attenuation) upon passing through a tissue of interest can be expressed by Equation 1:

$$I/I_o = e^{-\mu \chi} \tag{1}$$

where $I$ and $I_o$ are the transmitted and incident radiation intensities, respectively. The tissue thickness is $\chi$, and $\mu$ is the linear attenuation coefficient. In terms of interactions with the tissue of interest, $\mu$ increases with (i) an increase in tissue density and (ii) an increase in the mean atomic number, $Z_{eff}$, of the tissue. The relationship between $Z_{eff}$ and $\mu$ is a complex function due to atomic absorption edges.

The coefficient $\mu$ has three contributions at the clinical X-ray energies of 20–150 keV, each specifying an independent interaction of the X-ray radiation with matter: Rayleigh or coherent scattering ($\omega$), Compton or incoherent scattering ($\delta$), and the photoelectric event ($\tau$). Thus, $\mu$ is simply a summation of each type of interaction as expressed in Equation 2:

$$\mu = \omega + \delta + \tau \tag{2}$$

The contribution from coherent scattering is usually never more than 10% and generally considered negligible. Therefore the major contributors to X-ray attenuation are incoherent scattering and the photoelectric event, especially in the absence of contrast agent. In applications involving the use of X-ray contrast agent, however, $\tau$ is the dominant term. Equation 3 shows the proportionality of $\tau$ with $Z_{eff}$:

$$\tau \propto Z_{eff}^3 \tag{3}$$

Thus, in the presence of relatively high atomic weight iodinated contrast agents (Iodine, Z=53), the approximation in Equation 4 holds true:

$$\mu \propto Z_{eff}^3 \tag{4}$$

The proportionality of the linear attenuation coefficient to the cube of the effective atomic number explains the significant contrast enhancement that is seen in the final radiographs due to the presence of the contrast agent.

Angiography, or imaging of the blood vessels is one of the most common radiographic procedures. Typically, an aqueous commercial contrast agent formulation is injected rapidly via catheter directly into the blood stream. As the contrast agents in the injected material are carried through the blood vessels, their presence makes it possible to make images of those vessels.

Unfortunately, conventional contrast agents are absorbed out of the blood fairly quickly, so that they are only effective as imaging agents for about one minute. In addition, in the human circulatory system each blood cell circulates through the heart about once every two minutes. These two factors mean that it is desirable to inject conventional contrast agents very near to the area of interest and to acquire images almost immediately thereafter. Hence, when it is desired to acquire contrast agent-enhanced images of a patient's heart, it is necessary to use a catheter having its tip at or even in the heart. The catheter is typically inserted through a vessel in the thigh or groin and threaded through vessel until it reaches the heart. This is procedure is quite invasive and one that would be preferable to avoid. In addition, conventional contrast agents are often not suitable for use in the field because of the need to rapidly inject the contrast agent and obtain the image. For example, contrast agent-enhanced images of the blood flow through the hearts of stroke victims cannot be obtained in the field because of the impossibility of catheterizing the victim in the field and injecting the contrast agent near the heart.

Diffusion of the contrast agent through the intercellular junctions of the vascular endothelium, known as "extravasation" or "partial extravasation," occurs everywhere except where an organ/blood barrier exists (e.g. brain and prostate). Image quality is lost due to extravasation, which causes a loss of contrast between the blood vessels and the surrounding tissues. Contrast agents that do not allow or minimize extravasation are called "blood pool contrast agents."

Today's X-ray contrast agent have evolved the point where it is unlikely that simple modification of the R groups in FIG. 1 will lead to an improvement in tolerability or performance. Other applications that can be enhanced by the use of contrast agents include imaging of the urinary tract, sinuses, and salivary gland ducts. In each application, however, there continues to be a need for an effective, non-toxic contrast agent that will not be absorbed in to the body. As a result, new contrast agents are currently being investigated that may be delivered less invasively and have a longer circulation time in the body.

SUMMARY OF THE INVENTION

The present invention utilizes a fullerene scaffold to support an iodinated moiety and, preferably, a water solubilizing moiety for use as an improved contrast agent that can be delivered less invasively and have a longer circulation time in the body. The fullerene scaffold may comprise empty fullerenes or endohedral fullerenes.

In a preferred embodiment, the present invention comprises an agent for therapeutic or diagnostic treatment that includes a fullerene scaffold and an iodinated moiety bonded to the scaffold. In some embodiments, a plurality of water solubilizing moieties is also preferably bonded to the scaffold.

BRIEF DESCRIPTION OF THE DRAWINGS

For a detailed description of preferred embodiments of the invention, reference will now be made to the accompanying drawings wherein.

The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein.

DETAILED DESCRIPTION OF THE PREFERRED EMBODIMENTS

The present invention relates to adding iodinated moieties and optionally adding water-solubilizing moieties to fullerene scaffolds for contrast agent applications. The invention, is designed for, but not limited to, x-ray image enhancement in diagnostic medical imaging. The water-soluble material is particularly intended for intravenous or arterial injection, where its covalently bound iodine provides contrast in x-ray radiographs by attenuation of incident x-rays.

The present invention provides an effective x-ray contrast agent that is based upon the spherical scaffolding of $C_{60}$.

Among the potential advantages of a fullerene-based contrast agent are decreased systemic toxicity and increased blood-pool retention time. The latter advantage qualifies the material as a much sought after "blood-pool" agent, capable of providing contrast for extended periods of time relative to currently used agents.

Figure 2:
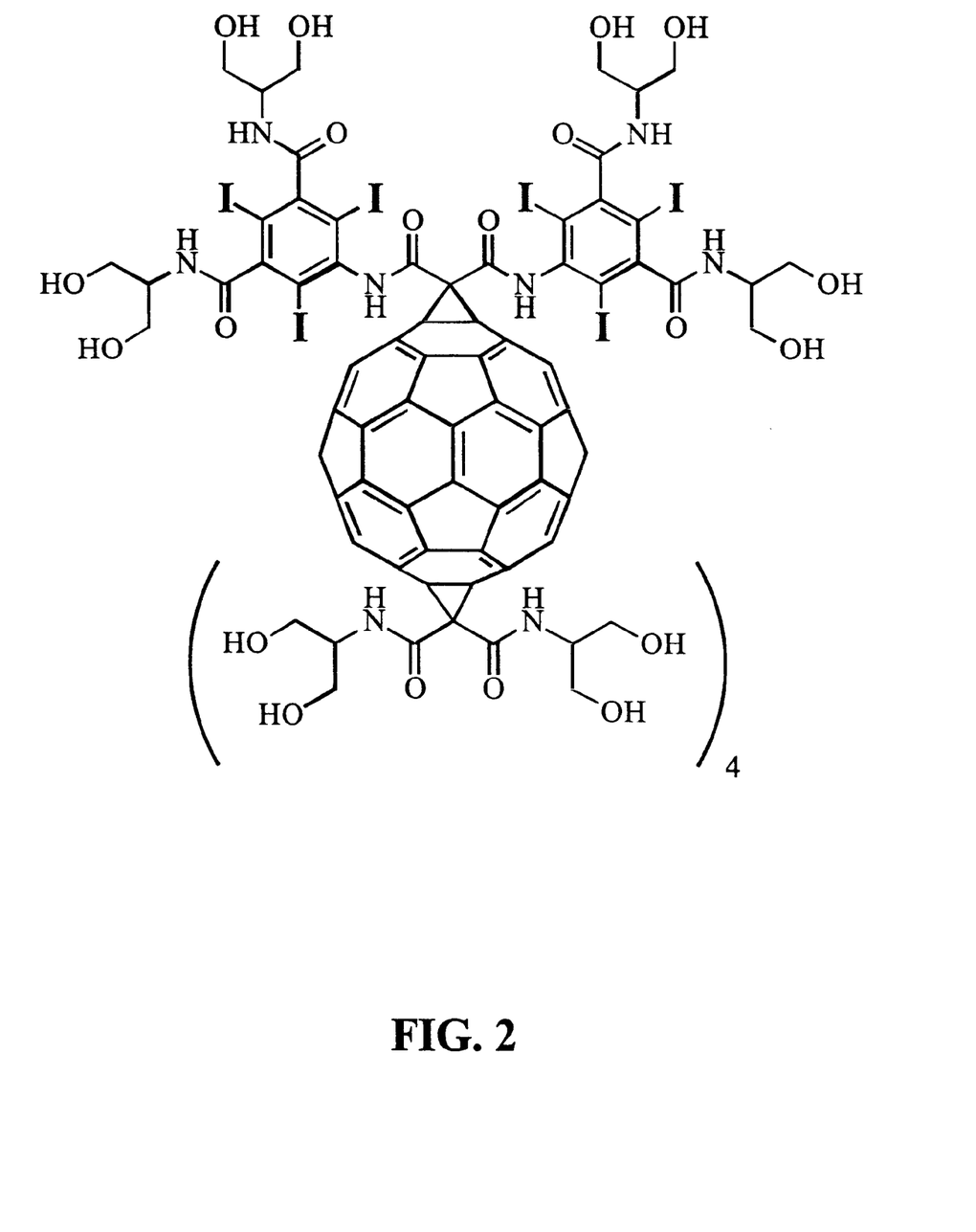
FIG. 2 is a schematic drawing of the chemical structure of an agent in accordance with a preferred embodiment of the present invention.

As shown in FIG. 2, a preferred embodiment of the present contrast agent includes two iodinated moieties and several water solubilizing moieties attached on opposite sides of a fullerene scaffold. The iodinated moieties confer radiopacity, while the water solubilizing moieties provide sufficient solubility in biological systems.

Fullerenes (i.e. $C_{60}$) were chosen as the scaffold for a number of reasons including: $C_{60}$ has been documented as having a low toxicity, $C_{60}$-based agents have a pseudo-spherical shape, the potential biodistribution of $C_{60}$-based agents throughout the body may provide the affinity to target specific tissues, and fullerenes have a large surface area and aromatic structure, which makes them particularly well-suited for the attachment of additional moieties. The pseudo-spherical shape is of special importance because agents with a reduced viscosity are produced, which increases the ease of injection into the body. Additionally, because $C_{60}$-based agents are larger than conventional contrast agents, such as Iohexol, the diffusion rate through various tissues is slower. As mentioned above, this qualifies fullerene-based contrast agents as a blood pool contrast agent. Lastly, fullerene-based agents can be targeted to specific tissues by appending tissue-targeting entities (i.e., small peptides or even antibodies) to the remaining unfunctionalized surface of the $C_{60}$ core.

Iodination of Fullerenes

Figure 3:
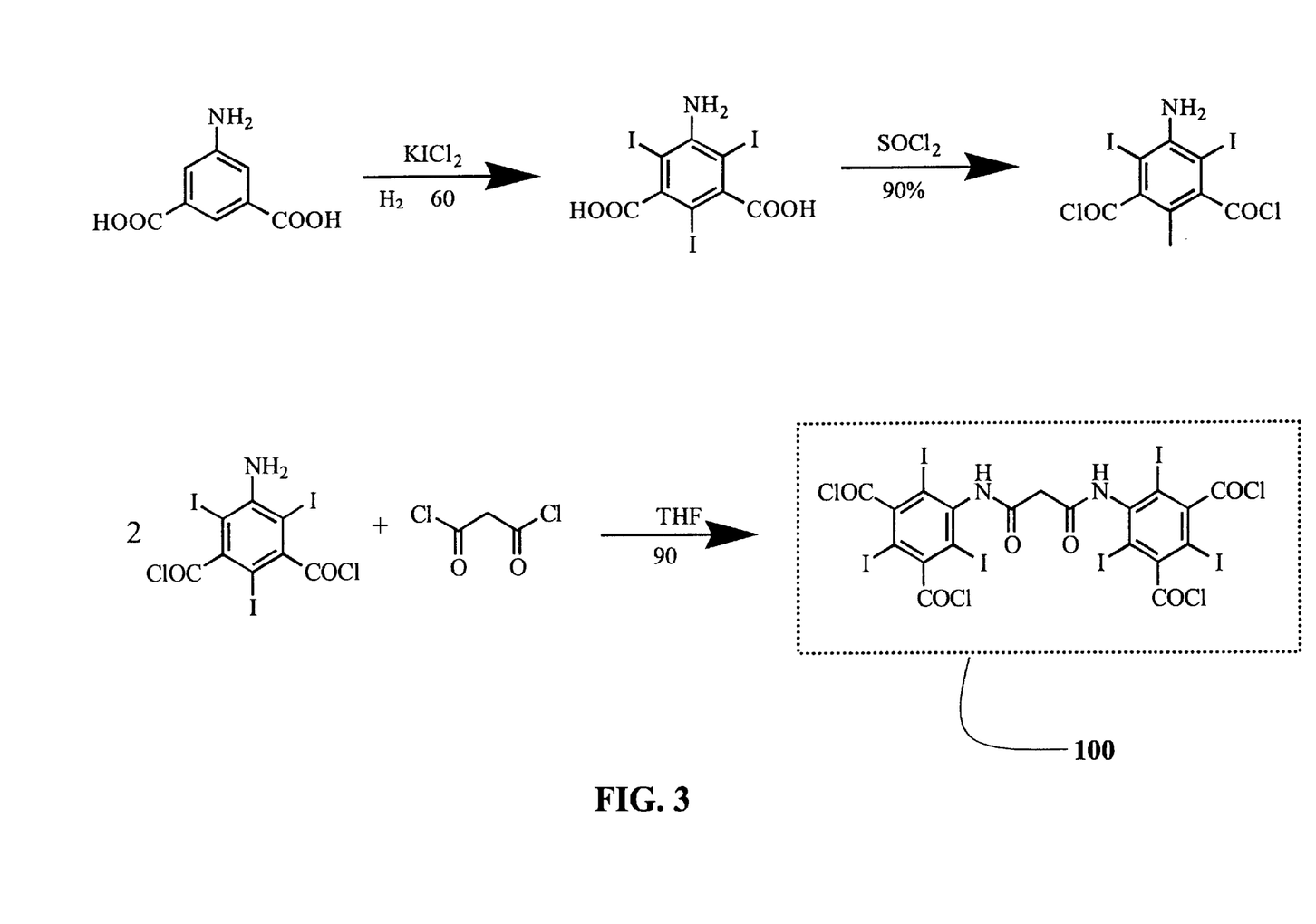
FIG. 3 is a schematic chemical diagram showing the synthesis of an iodinated moiety in accordance with a preferred embodiment of the present invention.

The iodination of fullerenes is preferably accomplished in four steps: (i) the synthesis of iodinated moieties, (ii) the protection of serinol, (iii) the attachment of serinols to iodinated moieties, and (iv) the attachment of iodinated serinols to fullerenes. Referring initially to FIG. 3, 5-aminoisophthalic acid is reacted in two steps with $KICl_2$ and water, and thionyl chloride under conditions effective to produce diacid dichloride. Diacid dichloride is condensed with malonyl dichloride in refluxing THF to yield an iodinated moiety, which is labeled 100.

Figure 4:
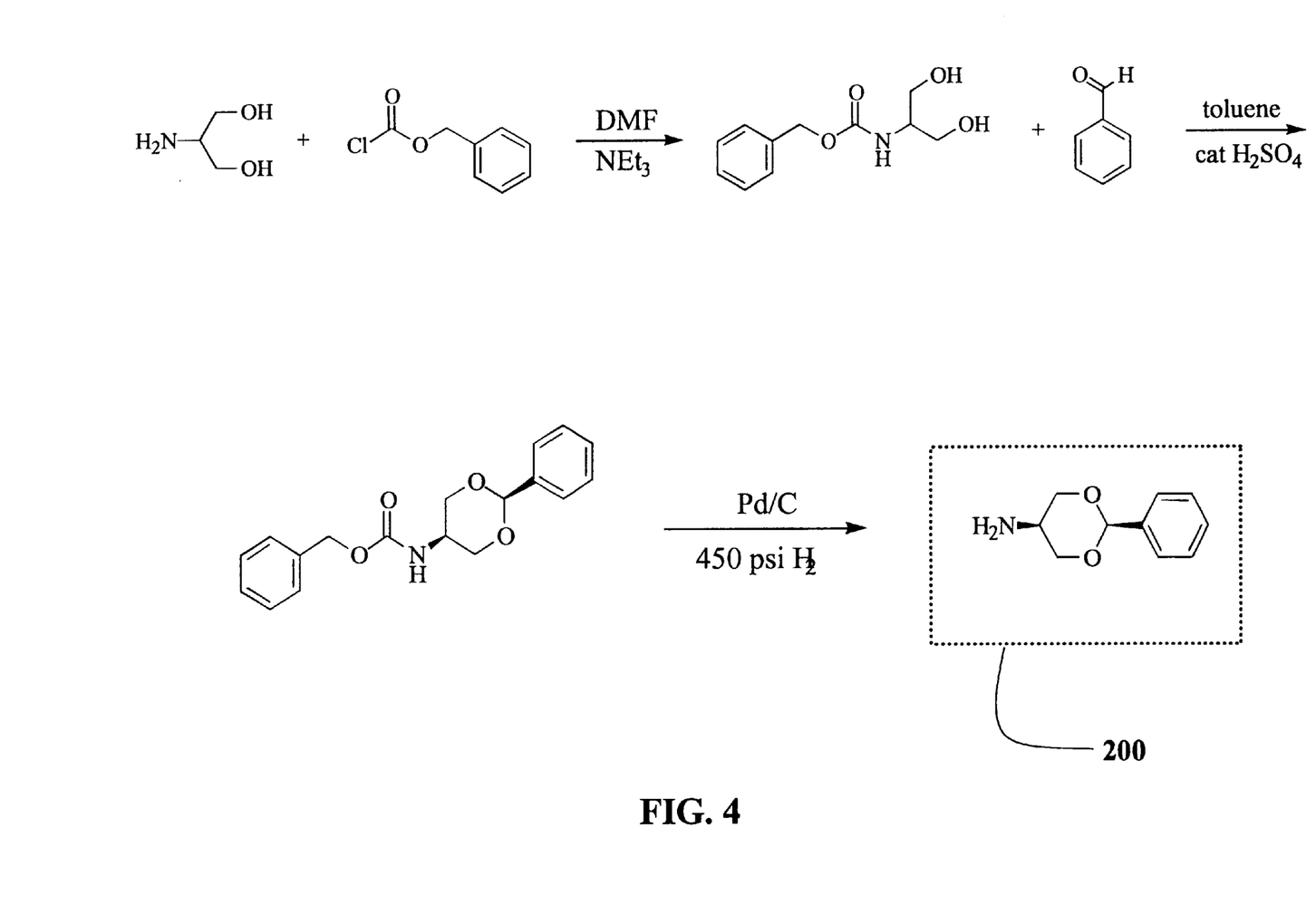
FIG. 4 is a schematic chemical diagram showing the protection of serinol in accordance with a preferred embodiment of the present invention.

Referring now to FIG. 4, in a preferred embodiment, serinol is protected, i.e. the amino groups are protected and prevented from reacting, by first reacting them with benzyl-chloroformate in DMF with $NEt_3$. The resulting compound is reacted with benzaldehyde in toluene with catalytic amounts of $H_2SO_4$ to form a benzylidene acetal. The amine can then be de-protected by catalytic hydrogenation to give a hydroxyl-protected serinol, labeled 200. Either the cis or trans protected serinol isomer, or both, can be used.

Figure 5:
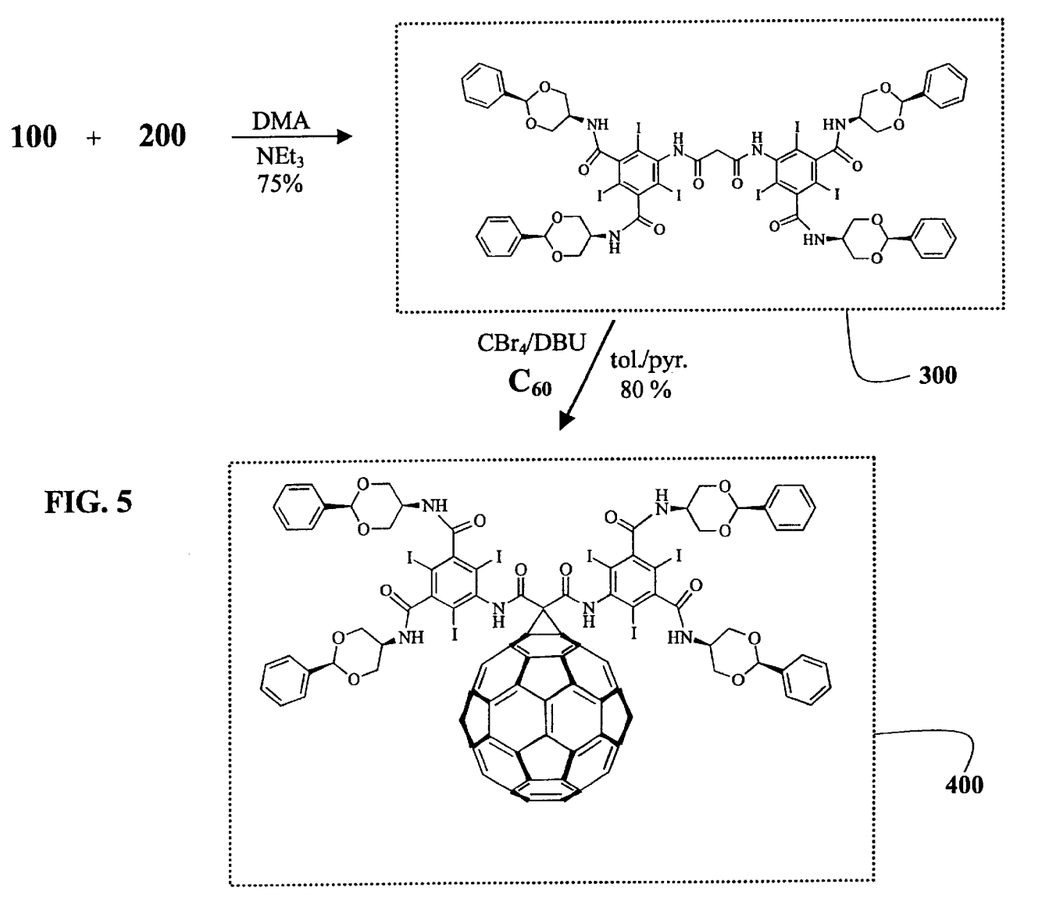
FIG. 5 is a schematic chemical diagram showing the attachment of serinols to an iodinated moiety in accordance with a preferred embodiment of the present invention.

As shown in FIG. 5, protected serinols are preferably reacted with an iodinated malonodiamide tetra-acid chloride in THF with $NEt_3$ to give the compound labeled 300 in FIG. 5. Preferably three protected serinols are reacted with iodinated malonodiamide tetra-acid chloride, and more preferably four protected serinols are reacted with iodinated malonodiamide tetra-acid chloride. Like $C_{60}$, 300 is soluble in non-polar solvents such as toluene.

Still referring to FIG. 5, the compound 300 is reacted with a fullerene, such as $C_{60}$, in a Bingel-type reaction. Bingel reactions are described in U.S. Pat. No. 5,739,376, which is incorporated herein by reference. Specifically, DBU and $CBr_4$ are added to a solution of 300 and $C_{60}$ in toluene to give an intermediate 400 comprising an iodinated fullerene having protected serinols. While the bromination of the intermediate has been described in-situ, it may alternatively occur in an isolated step. Preferably, the iodinated fullerene is monoadduct. In a preferred final step, the serinols are de-protected, such as by hydrolysis using $H_2SO_4$, to give the desired compound (shown post-solubization in FIG. 7). The desired compound is also an intermediate to which water-solubilizing groups attached as described below.

The preferred method, including the incorporation of serinols prior to the Bingel reaction, gives an acceptably high yield and a robust, convergent synthesis. In addition, the solubility of the serinol-protected intermediate allows further modification of the fullerene core.

Water Solubility

Because one expected use for the present invention is as an x-ray contrast agent, it is desirable to provide a form of the iodinated fullerene that is sufficiently water-soluble to be effective in vivo. This can be accomplished by optimizing the number and type of water-solubilizing substituents.

For example, the fullerene derivative (not shown) or its protected form 400 can be made water-soluble by attaching a plurality of alcohol protected serinol malonodiamide groups (such as those described above) also using a Bingel-type reaction. Specifically, serinol can be made to give the corresponding malonodiamide directly and attached to the fullerene using a Bingel-type reaction as described above. In this scheme, the serinols are prefereably protected using acetate, the benzylcarbamate/benzaldehyde scheme described above, or any other suitable protection mechanism. Fullerenes and iodinated fullerenes solubilized in this manner are non-ionic and therefore more suited for use in vivo.

Figure 6:
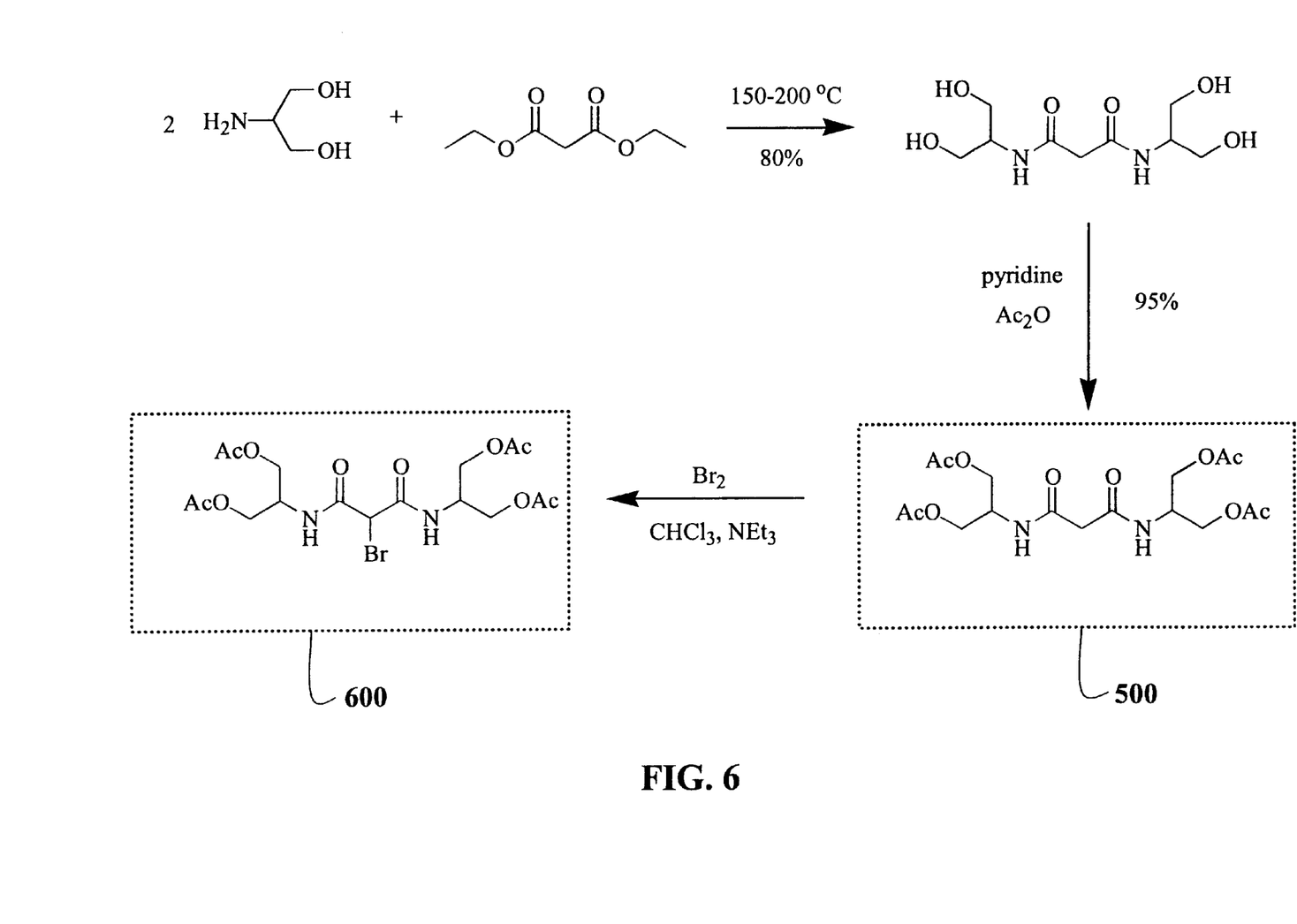
FIG. 6 is a schematic chemical diagram showing the synthesis of a water solubilizing moiety in accordance with a preferred embodiment of the present invention.

Referring now to FIG. 6, in a preferred embodiment, two equivalents of serinol (2-amino-1,3-propanediol) are condensed with diethylmalonate at elevated temperature, with the loss of ethanol, to give a corresponding malonodiamide. Esterification of the alcohol groups in pyridine/$Ac_2O$ is followed by electrophilic bromination at the central acidic carbon of the malonodiamide with $Br_2$ in $EtOAc/Net_3$. The bromomalonodiamide, is then appended to $C_{60}$ via a Bingel type reaction in the presence of DBU, in toluene or toluene/acetone to produce a desired intermediate, labeled 500. The stoichiometry can be varied depending on the degree of addition desired. The protective acetyl groups are then removed via $K_2CO_3$ in $CH_3OH/H_2O$, followed by removal of potassium, to yield desired the compound, labeled 600.

Figure 7:
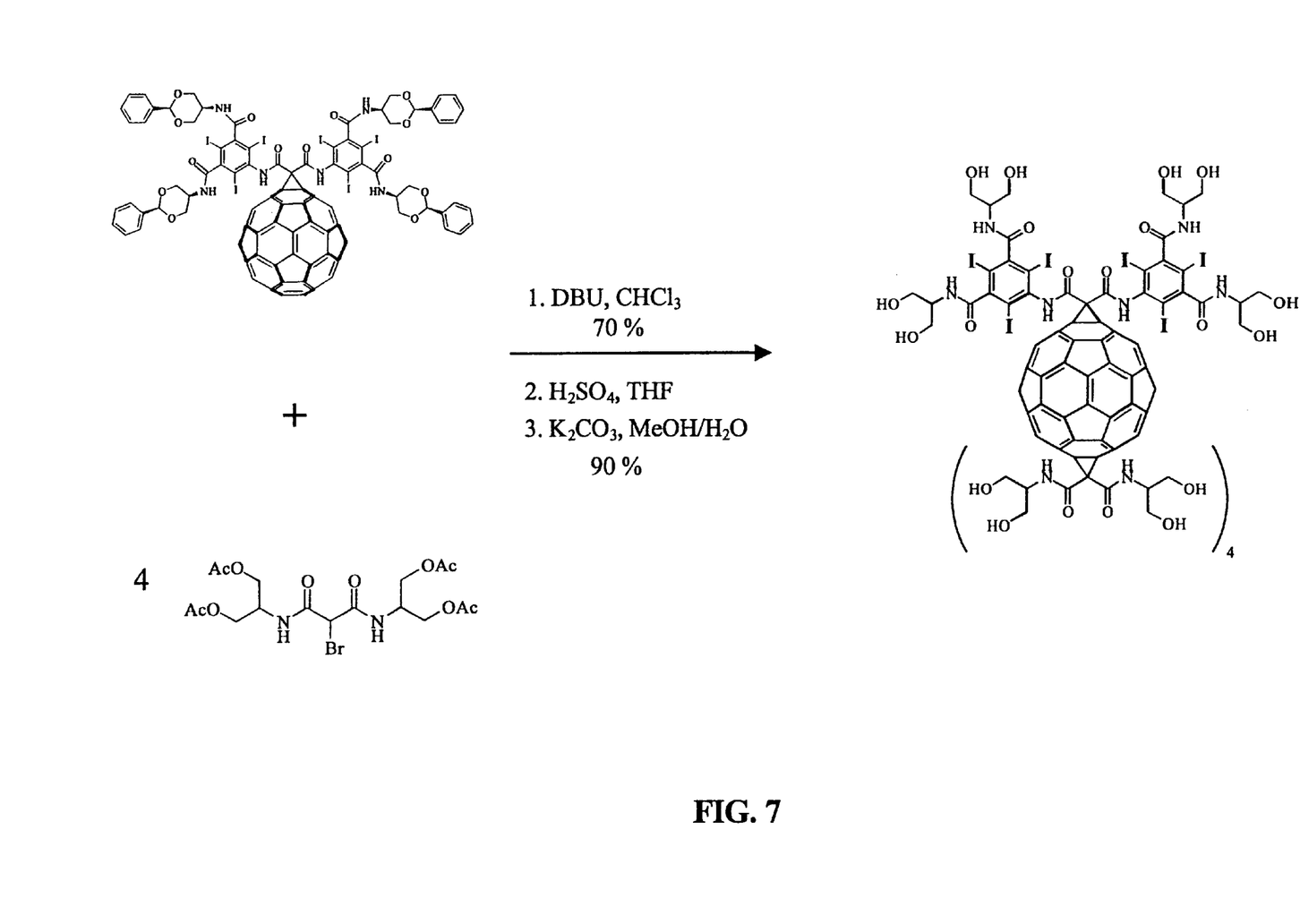
FIG. 7 is a schematic chemical diagram showing the synthesis of the agent in FIG. 2.

FIG. 7 shows the synthesis of combining the iodinated fullerene 400 with water solubilizing compound 600, followed by acetal and ester cleavage. As can be seen, the fullerene is covered with 1,3 hydroxyl groups, making it water-soluble.

An alternative technique for accomplishing the desired water solubility of the iodinated fullerenes is using the phase-transfer catalyst TBAOH (tetrabutylammonium hydroxide) and aqueous KOH and non-aqueous DMA/toluene reaction phases. This produces polyhydroxylated fullerenes, having at least ten and preferably at least 15 hydroxyl groups thereon, and having correspondingly enhanced water solubility. It is expected that these polyhydroxylated fullerenes linger in the circulatory system because of either self-aggregation or binding with blood proteins such as serum albumin. It is likely, therefore, that these and related polyhydroxylated fullerenes will also target the blood pool and exhibit the desired in vivo properties to allow long-term, e.g. one hour, x-ray angiography of the circulatory system.

In addition, the use of 1,3 diols may be used to increase the water solubility of the iodinated fullerenes. As is known, most diols are infinitely soluble in water.

Specifically, osmotically balanced compounds are preferred for use in in vivo applications. Fullerenes solubilized by the addition of serinols are more readily characterized than their polyhydroxylated counterparts, making them more desirable for use in vivo.)

As described above, it is believed that fullerenes and fullerols are substantially non-toxic. Where X-ray contrast agents are used as osmoactive agents in MRI contrast media, there are advantages to both ionic and non-ionic X-ray contrast agents. Thus, using ionic X-ray contrast agents, a lower concentration can be used to achieve the same osmotic effect. However, non-ionic agents are especially suitable as contrast media for administration to young children and persons with perfused or suspected perfusion of the GI system because of the general lower toxicity of non-ionic agents. Another advantage of the non-ionic agents is that they do not precipitate in the stomach.

The present technique for iodinating and water solubilizing fullerenes can be used to advantage with various known x-ray contrast agents. These are preferably iopamidol (see BE-A-836355), iohexol (see GB-A-1548594), but also including but are not limited to other agents disclosed and described in the art, such as non-ionic X-ray contrast agents for example, metrizamide (see DE-A-2031724), iotrolan (see EP-A-33426), iodecimol (see EP-A-49745), iodixanol (see EP-A-108638), ioglucol (see U.S. Pat. No. 4,314,055), ioglucomide (see BE-A-846657), ioglunioe (see (DE-A-2456685), iogulamide (see BE-A-882309), iomeprol (EP-A-26281), iopentol (see EP-A-105752), iopromide (see DE-A-2909439), iosarcol (see DE-A-3407473), iosimide (see DE-A-3001292), iotasul (see EP-A-22056), iovarsul (see EP-A-83964) and ioxilan (see WO87/00757).

In summary, a new synthetic methodology for iodinating and water solubilizing fullerene materials has been developed. The resulting fullerene derivatives are exceedingly soluble in water without significant pH dependence. This effective approach for water-solubilizing fullerene-based materials leads to well-defined, biologically compatible products and is generally applicable to empty fullerenes, as well as to endohedral metallofullerenes, $M@C_n$, with M being any one of several medically interesting metal ions, including, but not limited to lanthanides such as gadolinium.

Endohedral metallofullerenes can be solubilized according to the methods described above. For $C_{60}$, it is preferable to use at least five protected serinols to react with iodinated malonodiamide tetra-acid chloride. For $C_{82}$, it is preferable to use at least eight protected serinols to react with iodinated malonodiamide tetra-acid chloride.

In addition to x-ray image enhancement in diagnostic medical imaging, the present contrast agents may be used in therapeutic applications such as in the treatment of tumors. X-ray therapy is similar to Gamma Knife radiation therapy, the technology currently used to treat tumors. In Gamma Knife radiation therapy, the radiation delivered by the Gamma Knife actually destroys the DNA in the tumor cells so that they are no longer able to grow and reproduce. When the cell matures and is unable to replicate itself, it simply dies. Due to this inability to replace dying cells, the tumor's growth is halted.

As described above, by appending tissue-targeting entities for specific tissues (i.e. tumors) to the present contrast agents, and enabling the contrast agents to diffuse across the cell walls of the specific tissues, a sufficient amount of energy may be generated via radiation to destroy the DNA in the cells.

While preferred embodiments of this invention have been shown and described, modifications thereof can be made by one skilled in the art without departing from the spirit or teaching of this invention. It will be understood that, unless otherwise indicated, method steps may be carried out in any order. Further, unless otherwise indicated, methods steps may be carried out concurrently. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A composition for therapeutic or diagnostic treatment comprising:
    a fullerene scaffold; and
    an iodinated x-ray contrast agent bonded to the scaffold.
2. The composition of claim 1 further comprising a water solubilizing moiety bonded to the scaffold.
3. The composition of claim 2 wherein the water solubilizing moiety is selected from the group consisting of serinol malonodiamides, hydroxyls, and 1,3-diols.
4. A composition for therapeutic or diagnostic treatment comprising:
    a fullerene scaffold;
    an iodinated moiety bonded to the scaffold;
    a water solubilizing moiety bonded to the scaffold, wherein the water solubilizing moiety is selected from the group consisting of alcohol protected serinol malonodiamides.
5. The composition of claim 2 wherein said fullerene scaffold comprises an empty fullerene.
6. The composition of claim 2 wherein said fullerene scaffold comprises an endohedral fullerene.
7. The composition of claim 6 wherein said endohedral fullerene comprises metal ions selected from the group containing lanthanide metals.
8. The composition of claim 7 wherein said metal ions comprise gadolinium.
9. The composition of claim 2 wherein said iodinated x-ray contrast agent provides radiopacity.
10. The composition of claim 9 wherein said x-ray contrast agent provides x-ray image enhancement.
11. The composition of claim 2 wherein said water solubilizing moiety provides solubility in biological systems.
12. The composition of claim 2 wherein said composition is capable of intravenous or arterial injection.
13. A method for iodinating a fullerene scaffold comprising:
    a) synthesizing iodinating moieties;
    b) protecting serinols, forming protected serinols;
    c) attaching the protected serinols to the iodinated moieties, forming iodinated serinols; and
    d) attaching the iodinated serinols to the fullerene scaffold.
14. The method of claim 13 wherein the protected serinols comprise a cis, trans, or cis-trans isomer.
15. The method of claim 13 wherein step d is accomplished via a Bingel-type reaction.
16. The method of claim 13 further comprising de-protecting the serinols.
17. The method of claim 13 wherein the fullerene scaffold comprises an empty fullerene.
18. The method of claim 17 wherein the fullerene scaffold essentially comprises $C_{60}$.
19. The method of claim 18 wherein at least three iodinated serinols are attached to the fullerene scaffold.
20. The method of claim 18 wherein at least four iodinated serinols are attached to the fullerene scaffold.
21. The method of claim 13 wherein the fullerene scaffold comprises an endohedral fullerene.
22. The method of claim 21 wherein the fullerene scaffold essentially comprises $C_{60}$.
23. The method of claim 22 wherein at least five iodinated serinols are attached to the fullerene scaffold.
24. The method of claim 21 wherein the fullerene scaffold essentially comprises $C_{82}$.
25. The method of claim 24 wherein at least eight iodinated serinols are attached to the fullerene scaffold.
26. A method of water solubilizing a fullerene scaffold comprising attaching a plurality of serinol malonodiamide groups to the fullerene scaffold.
27. The method of claim 26 wherein the alcohol groups of the serinol are protected.
28. The method of claim 26 wherein the plurality of serinol malonodiamide groups is attached to the fullerene scaffold via a Bingle-type reaction.
29. The method of claim 27 further comprising de-protecting the alcohol groups.
30. A method for iodinating and water solubilizing a fullerene scaffold comprising:
    a) synthesizing iodinating moieties;
    b) protecting serinols, forming protected serinols;
    c) attaching the protected serinols to the iodinated moieties, forming iodinated serinols;
    d) attaching the iodinated serinols to the fullerene scaffold; and
    e) attaching a plurality of water solubilizing moieties to the fullerene scaffold.
31. The method of claim 30 wherein the water solubilizing moieties are selected from the group consisting of alcohol protected serinol malonodiamides.
32. The method of claim 30 further comprising de-protecting the serinols.
33. A method for providing diagnostic treatment to a patient comprising administering to said patient a radiopaque effective amount of a composition comprising a fullerene scaffold and an iodinated x-ray contrast agent.
34. The method of claim 33 wherein the composition further comprises water solubilizing moieties.
35. A method for providing diagnostic treatment to a patient comprising administering to said patient a radiopaque effective amount of a contrast agent comprising a fullerene scaffold, an iodinated moiety, and water solubilizing moieties, wherein the water solubilizing moieties are selected from the group consisting of serinol malonodiamides.
36. A method of making a blood pool agent, comprising:
    providing a fullerene scaffold;
    bonding an iodinated x-ray contrast agent to the scaffold; and
    bonding a plurality of water solubilizing moieties to the scaffold.
37. A tissue-specific agent comprising:
    a fullerene scaffold;
    an iodinated x-ray contrast agent bonded to the scaffold; and
    a tissue-targeting moiety bonded to the scaffold.
38. The tissue-specific agent of claim 37 further comprising a plurality of water solubilizing moieties bonded to the scaffold.

* * * * *